United States Patent [19]

Prasad

[11] Patent Number: 4,459,263
[45] Date of Patent: Jul. 10, 1984

[54] COBALT-CHROMIUM DENTAL ALLOYS CONTAINING RUTHENIUM AND ALUMINUM

[75] Inventor: Arun Prasad, Cheshire, Conn.

[73] Assignee: Jeneric Industries, Inc., Wallingford, Conn.

[21] Appl. No.: 415,809

[22] Filed: Sep. 8, 1982

[51] Int. Cl.³ .............................................. C22C 5/00
[52] U.S. Cl. ................................................... 420/437
[58] Field of Search ...................................... 420/1437

[56] References Cited

U.S. PATENT DOCUMENTS

| | | | |
|---|---|---|---|
| 1,283,264 | 10/1918 | Mowrey | 75/134 |
| 2,089,587 | 8/1937 | Tesceda | 32/2 |
| 2,165,849 | 7/1939 | Grossman | 75/171 |
| 2,570,355 | 10/1951 | Low | 75/171 |
| 2,920,956 | 1/1960 | Nisbet et al. | 75/171 |
| 3,134,670 | 5/1964 | Prosen | 75/171 |
| 3,304,177 | 2/1967 | Wlodek | 75/171 |
| 3,399,058 | 8/1968 | Roush | 75/170 |
| 3,413,723 | 12/1968 | Wagner et al. | 32/8 |
| 3,464,817 | 9/1969 | Griffiths | 75/171 |
| 3,667,936 | 6/1972 | Katz | 75/134 N |
| 3,749,570 | 7/1973 | Lyon | 75/171 |
| 3,756,809 | 9/1973 | Asgar | 75/134 F |
| 3,767,391 | 10/1973 | Tuccillo et al. | 75/134 |
| 3,802,875 | 4/1974 | Klein et al. | 75/171 |
| 3,802,934 | 4/1974 | Augustine, Jr. et al. | 148/32.5 |
| 3,819,366 | 6/1974 | Katz | 75/172 R |
| 3,837,834 | 9/1974 | Mohammed | 75/134 |
| 3,914,867 | 10/1975 | Manning et al. | 32/2 |
| 3,981,723 | 9/1976 | Tuccillo | 75/165 |
| 4,007,040 | 2/1977 | Kropp | 75/165 |
| 4,229,215 | 10/1980 | Prosen | 75/134 |
| 4,253,869 | 3/1981 | Prosen | 75/134 |
| 4,255,190 | 3/1981 | Prosen | 75/134 |
| 4,263,045 | 4/1981 | Prosen | 75/134 |

FOREIGN PATENT DOCUMENTS

| | | | |
|---|---|---|---|
| 1240671 | 11/1967 | Fed. Rep. of Germany | 75/170 |
| 1295847 | 5/1969 | Fed. Rep. of Germany | 75/170 |
| 1608156 | 12/1970 | Fed. Rep. of Germany | |
| 2615755 | 12/1976 | Fed. Rep. of Germany | |

OTHER PUBLICATIONS

Ullmann Enzyklopädie der Technischen Chemie, 4th edition, vol. 10, p. 6 and vol. 14, pp. 281, 282 and 284.
European Patent Publication No. EP 0 041 938 A2 (published Dec. 16, 1981).

*Primary Examiner*—Peter D. Rosenberg
*Attorney, Agent, or Firm*—Barry Kramer

[57] ABSTRACT

A cobalt-chromium dental alloy for use in porcelain-fused-to-metal restorations consisting essentially of about:

| Element | Weight Percent |
|---|---|
| Cobalt | 40–60 |
| Chromium | 20–30 |
| Ruthenium | 5–15 |
| Aluminum | 1–4 |
| Yttrium | 0–0.15 |
| Tungsten | 0–15 |
| Molybdenum | 0–6.5 |
| Niobium | 0–3.0 |
| Zirconium | 0–0.25 |
| Manganese | 0–1.5 | wherein the sum of the constituents equal 100% and the sum of the tungsten and molybdenum constituents minus the sum of the ruthenium, niobium and zirconium constituents is less than about 5%. These alloys exhibit outstanding physical and chemical properties, including the formation of a tenacious bond with porcelain without the need for a separate bonding agent, and can be used advantageously as a substitute for alloys having a high proportion of precious metals as well as for nickel-chromium-based alloys in the fabrication of porcelain-veneered fixed bridgework and crowns.

5 Claims, No Drawings

COBALT-CHROMIUM DENTAL ALLOYS CONTAINING RUTHENIUM AND ALUMINUM

FIELD OF THE INVENTION

This invention relates to cobalt-chromium dental alloys. More particularly, this invention relates to cobalt-chromium alloys containing ruthenium and aluminum, such that the resulting alloys exhibit outstanding physical, thermal and oxidation properties thereby rendering such alloys suitable for use in porcelain-fused-to-metal restorations without the need for a bonding agent in the fabrication of such restorations.

BACKGROUND OF THE INVENTION

Numerous criteria must be met by an alloy to be used in the fabrication of prosthetic dental appliances such as procelain-veneered fixed bridgework and crowns. For example, the alloy must be tissue tolerant, tarnish resistant, corrosion resistant and non-toxic.

In addition, the alloy should form a protective and adherent oxide on its surface during torch melting and during the porcelain-firing cycle which does not grow dramatically in thickness. The oxides formed must be compatible with the porcelain; otherwise, they may affect the thermal expansion of the interfacial porcelain. Still further, the oxides should not discolor the porcelain. Most preferably, the oxide should be able to bond the porcelain to the alloy without the need for a separate bonding agent.

The alloy must also have a coefficient of thermal expansion slightly higher than that of the porcelains currently available on the market thereby placing the porcelain under compression and minimizing the stresses formed at the interface.

The alloy also should be shape-stable with porcelain application, possess adequate strength for function, produce an acceptable fit and be solderable. Finally, it should possess a high modulus of elasticity, high-yield strength and hardness and be easily cast, ground and polished using techniques conventionally employed in dental laboratories.

The criteria which govern the selection of a suitable alloy for use in the preparation of porcelain-veneered fixed bridgework and crowns are quite different from the criteria involved in selecting alloys for use in the fabrication of partial dentures which generally are not used in conjunction with porcelain. These criteria, to a large extent, have heretofore been met by alloys having a high precious metal content. Such alloys have contained gold, platinum, palladium, silver, indium, tin, gallium, zinc, and the like, and trace metals. Formulations of alloys of this type are set forth in U.S. Pat. Nos. 1,283,264, 3,413,723, 3,667,936, 3,767,391, 3,819,366, 3,981,723 and 4,007,040.

With the ever increasing and fluctuating cost of precious metals and the superior physical properties and technological advantages offered by nickel-chrome-base alloys, such alloys have become widely used as an alternative to precious alloys in dentistry. These alloys generally utilize tin, gallium and the like to impart specific physical characteristics. Typical of such alloys are those described in U.S. Pat. Nos. 2,089,587, 3,304,177, 3,464,817, 3,749,570 and 3,914,867.

Currently, there is growing concern about nickel being an allergen and beryllium being a toxic element. Although much data are still needed, there is an apparent need for an alloy which contains neither nickel nor beryllium, has a low precious metal content and yet meets the above criteria.

A number of cobalt-chromium base alloys with and without nickel and/or beryllium have heretofore been employed in dentistry for the fabrication of removable partials, crowns and bridgework. Typical of such alloys are those described in U.S. Pat. Nos. 3,756,809, 3,802,875, 3,802,934 and 3,837,838. However, their compositions and physical and thermal properties have limited their use for porcelain-veneered crown and bridgework.

Cobalt-chromium based alloys having a variety of compositions and said to be useful for porcelain-fused-to-metal restorations have been disclosed in U.S. Pat. Nos. 4,229,215, 4,253,869, 4,255,190 and 4,263,045. Of these, U.S. Pat. Nos. 4,253,869 and 4,255,190 describe alloys including cobalt, chromium and ruthenium. None of the alloys disclosed in these patents, however, includes aluminum or aluminum/yttrium, which, in accordance with the present invention, has been found to significantly improve the oxide formed on the alloy and the reactivity of the alloy with the melting crucible and the casting investment.

SUMMARY OF THE INVENTION

Accordingly, it is an object of the present invention to provide an alloy with a low precious metal content which exhibits many of the properties of metal alloys having a high precious metal content heretofore considered desirable in the fabrication of porcelain-veneered fixed bridgework and crowns.

It is another object of the present invention to provide an alloy free of nickel and/or beryllium.

These as well as other objects and advantages are accomplished by the present invention which provides chromium-cobalt alloys containing ruthenium and aluminum which are significantly different from prior chromium-cobalt alloys heretofore employed in the fabrication of prosthetic dental appliances. The chromium-cobalt alloys of the present invention exhibit melting characteristics enabling the use of standard natural gas/oxygen torches conventionally used in dental laboratories. Moreover, the alloys of the present invention form greatly improved oxides during torch melting and the procelain firing process, which oxides bond the alloy to the porcelain without the need for a separate bonding agent. Accordingly, the alloys of the present invention can be successfully employed in the fabrication of porcelain-veneered fixed bridgework and crowns in lieu of alloys having a high precious metal content and alloys having nickel and/or beryllium heretofore employed.

The cobalt-chromium alloys of the present invention consist essentially of about:

| Element | Weight Percent |
|---|---|
| Cobalt | 40–60 |
| Chromium | 20–30 |
| Ruthenium | 5–15 |
| Aluminum | 1–4 |
| Yttrium | 0–0.15 |
| Tungsten | 0–15 |
| Molybdenum | 0–6.5 |
| Niobium | 0–3.0 |
| Zirconium | 0–0.25 |
| Manganese | 0–1.5 | wherein the sum of the constituents equals 100% and the sum of the tungsten and molybdenum constituents minus the sum of the ruthenium, niobium and zirconium constituents is less than about 5%. These alloys exhibit outstanding physical and chemical properties, including the formation of a tenacious bond with porcelain without the need for a separate bonding agent, and can be used advantageously as a substitute for alloys having a high proportion of precious metals as well as for nickel-chromium-based alloys in the fabrication of porcelain-veneered fixed bridgework and crowns.

Preferred formulations of alloys following the teachings of the invention are given in Table I.

TABLE I

| Element | Weight Percent | | | |
| --- | --- | --- | --- | --- |
| | 1 | 2 | 3 | 4 |
| Co | 54.85 | 53 | 55 | 60 |
| Cr | 25 | 23 | 25 | 25 |
| Ru | 5 | 10 | 5 | 5 |
| Al | 2.9 | 3.9 | 2.9 | 3.9 |
| Y | 0.1 | 0.1 | 0.1 | 0.1 |
| W | 10 | 10 | 10 | — |
| Mo | — | — | — | 5 |
| Nb | 2 | — | 2 | — |
| Zr | 0.15 | — | — | — |
| Mn | — | — | — | 1.0 |

DESCRIPTION OF THE PREFERRED EMBODIMENTS

The cobalt-chromium alloys of the present invention are especially suited for use in the fabrication of prosthetic dental appliances since the cobalt in the alloy imparts characteristics to the alloy which closely correspond to those of alloys having a high precious metal content, especially the coefficient of thermal expansion which is quite close to that of gold. The chromium in the alloy provides enhanced corrosion and tarnish resistance. Chromium in amounts of from about 20% to 30% acts as a solid solution strengthener and provides a convenient means of adjusting the thermal expansion characteristics of the alloy to conform to the variations encountered upon use of different commercial porcelains.

The incorporation of aluminum or aluminum/yttrium in the alloy has been found to be critical in meeting the various criteria imposed on alloys which are useful in the preparation of porcelain-fused-to-metal restorations. In particular, when aluminum or aluminum/yttrium is included in the alloy, it has been found that porcelain readily and firmly bonds to the alloy without the need for a separate bonding agent. Also, the aluminum or aluminum/yttrium lowers the casting temperature and enhances the oxidation resistance of the alloy. This increased oxidation resistance helps prevent the formation of a thick oxide layer on the casting during the porcelain application process. This is important because thick oxide layers are fragile and impair the strength of the porcelain-metal bond in porcelain-fused-to-metal dental restorations.

The alloys of the present invention also have been found to be relatively unreactive with the crucible during torch melting. The alloys leave a thin slag which can be lifted up easily. It is believed that the aluminum, with the aid of yttrium, when used, leads to this behavior.

Further, the alloys of the invention produce castings having cleaner surfaces than those achieved with prior cobalt-chromium alloys containing ruthenium. This improvement is believed to result from the fact that the alloy reacts less with the investment and thus, after the investment is removed, the surface of the casting is both smoother and more characteristic of the metal of the alloy, rather than of a reaction product of the alloy with the investment. Again, it is believed that the aluminum, plus to some extent the yttrium, when used, leads to this result.

Also, the oxide formed on the alloys of the invention during degassing and during the porcelain firing process has a better color than the oxide formed on prior art cobalt-chromium alloys. In particular, the oxide formed during degassing is light grey in color and this color does not darken during the application of the porcelain. In contrast, prior art cobalt-chromium alloys form, during degassing, a greenish oxide which darkens during the subsequent porcelain firing process. Again, it is believed that the aluminum or aluminum/yttrium leads to this improvement.

To adjust the thermal expansion of the alloy varying amounts of niobium and tungsten/molybdenum are used. Alternatively, tantalum and vanadium can be used instead of tungsten and molybdenum. Ruthenium also has an effect on the expansion behavior. All of these elements lower the coefficient of thermal expansion of the alloy.

The ruthenium, niobium and zirconium in the alloy serve to make the alloy more ductile. Tungsten and molybdenum, however, as well as chromium, embrittle the alloy. It has been found that alloys having a suitable ductility for porcelain-fused-to-metal restorations are achieved for chromium concentrations in the range of about 20 to about 30% when the sum of the tungsten and molybdenum concentrations minus the sum of the ruthenium, niobium and zirconium concentrations is kept below about 5%. Further, a balance between the amounts of ruthenium, niobium and zirconium on one hand and aluminum or aluminum/yttrium on the other hand must be maintained. This is so because it has been found that aluminum or aluminum/yttrium tends to lessen the improvement in ductitily achieved through addition of ruthenium, niobium and zirconium. Specifically, it has been found that the aluminum concentration must be kept below about 4% and the yttrium concentration below about 0.15%.

The alloys of the present invention can be prepared by conventional alloying techniques. If desired, alloying can be done in air, under vacuum or by employing a blanket of an inert gas such as argon. The latter precautions, although preferred, are not considered essential. Generally, the major alloy constituents are melted first, such as through use of an induction furnace, taking care to maintain a homogeneous distribution of chromium in the melt by overcoming its tendency to float to the surface. After the cobalt and chromium have been melted and are well dispersed, tungsten, when used, can be added. Thereafter, the remaining alloy constituents can be added in either elemental form or as a preformed alloy with cobalt or chromium. Once the alloy melt is prepared and ingots cast therefrom, the remelting of the alloy ingot may be accomplished using a standard natural gas/oxygen torch or induction melting equipment.

The alloys of the present invention can be used instead of alloys having a high proportion of precious metal or alloys based on nickel and chromium without requiring any significant changes in technique other than as presently practiced in a dental laboratory. The castings obtained with the alloys of the present invention exhibit smooth non-porous surfaces. The absence of nickel and beryllium precludes the need for any special handling precautions.

The following examples further illustrate the criticalities of the alloy composition of the present invention. Unless otherwise specified, all percentages and parts are by weight.

EXAMPLES 1-12

The alloy compositions set forth in Table II were prepared in the manner set forth above.

TABLE II

| Element | 1 | 2 | 3 | 4 | 5 | 6 | 7 | 8 | 9 | 10 | 11 | 12 |
|---------|------|----|----|----|----|-------|------|----|----|----|----|----|
| Co | 54.85 | 53 | 55 | 60 | 56 | 52.83 | 58.9 | 52 | 52 | 53 | 55 | 56 |
| Cr | 25 | 23 | 25 | 25 | 26 | 22 | 26 | 25 | 25 | 23 | 25 | 26 |
| Ru | 5 | 10 | 5 | 5 | 5 | 10 | 5 | 5 | 5 | 10 | 5 | 5 |
| Al | 2.9 | 3.9 | 2.9 | 3.9 | 2.9 | — | — | 5.9 | 6 | 3.9 | 3 | 2.9 |
| Y | 0.1 | 0.1 | 0.1 | 0.1 | 0.1 | — | 0.1 | 0.1 | — | 0.1 | 1 | 0.1 |
| W | 10 | 10 | 10 | — | 8 | 10 | 10 | 10 | 10 | — | 9 | 10 |
| Mo | — | — | — | 5 | — | 2 | — | — | — | 10 | — | — |
| Nb | 2 | — | 2 | — | 2 | 0.5 | — | 2 | 2 | — | 2 | — |
| Zr | 0.15 | — | — | — | — | — | — | — | — | — | — | — |
| Mn | — | — | — | 1 | — | 0.5 | — | — | — | — | — | — |
| B | — | — | — | — | — | 0.17 | — | — | — | — | — | — |
| Fe | — | — | — | — | — | 1 | — | — | — | — | — | — |
| Cu | — | — | — | — | — | 1 | — | — | — | — | — | — |

The physical properties of alloys 1-12 and the percent thermal expansion values ($K_T$) at 500° C. for alloys 1-4 are given in Table III. The physical properties were measured using an Instron machine. The $K_T$ values were measured using a Theta differential dilatometer, where the reference temperature was 30° C., the rate of temperature climb was 3° C./minute and the reference standard was pure platinum.

TABLE III

| Alloy | $K_T$ | Yield Strength | Ultimate Tensile Strength | Elongation |
|-------|-------|----------------|---------------------------|------------|
| 1 | .6398 | 87,000 psi | 100,000 psi | 8% |
| 2 | .6480 | 90,000 psi | 108,000 psi | 6% |
| 3 | .6398 | 97,000 psi | 111,000 psi | 7% |
| 4 | .6726 | 84,000 psi | 100,000 psi | 6% |
| 5 | — | 101,000 psi | 123,000 psi | 6% |
| 6 | — | 104,000 psi | 145,000 psi | 14% |
| 7 | — | 61,000 psi | 61,000 psi | 0% |
| 8 | — | too brittle to test | | |
| 9 | — | too brittle to test | | |
| 10 | — | 34,000 psi | 34,000 psi | 0% |
| 11 | — | 62,000 psi | 62,000 psi | 0% |
| 12 | — | 73,000 psi | 89,000 psi | 3% |

Alloys 1-5, which follow the teachings of the present invention, were each found to have tensile strength and elongation values within the range which is suitable for porcelain-fused-to-metal restorations. Also, each of these alloys was found to have an oxide coating especially suitable for bonding to porcelain.

The remaining alloys (alloys 6-12) illustrate the criticality of the compositions of the alloys of the present invention as well as their improved properties relative to prior art alloys for porcelain-fused-to-metal restorations.

Thus, alloy 6, which was formulated in accordance with U.S. Pat. No. 4,253,869, shows the importance of having aluminum or aluminum/yttrium in the alloy. This alloy was observed to react with the melting crucible and the investment, which is undesirable. In contrast, each of alloys 1-5, which follow the teachings of the invention, were inert with respect to the melting crucible and the investment. Not having aluminum or aluminum/yttrium, as discussed above, alloy 6 was somewhat more ductile, i.e., it had a higher elongation.

The importance of aluminum in preventing reaction of the alloy with the crucible and the investment is further illustrated by alloys 6 and 7. Both of these alloys, which contain no aluminum, were found to react with the crucible and the investment.

The upper limit on the amount of aluminum is illustrated by alloys 3, 8 and 9. Alloy 9 which has 6% aluminum was found to be too brittle to use as a dental alloy for porcelain-fused-to-metal restorations. Alloy 8, which was also too brittle, shows that the addition of yttrium will not cure the brittleness problem at high aluminum. Alloy 3, on the other hand, which has the same composition as alloys 8 and 9 except for its aluminum concentration, was not brittle. This alloy has an aluminum concentration below the upper limit of 4%.

Alloys 4 and 10 illustrate the importance of keeping the concentration of molybdenum below about 6.5%. Alloy 10 with 10% molybdenum was found to be too brittle, while alloy 4 with 5% molybdenum had a 6% elongation which is commercially acceptable.

Alloys 3 and 11 illustrate the effect of high yttrium. Alloy 11 with 1% yttrium was found to be too brittle. Alloy 3 which has essentially the same formulation but with 0.1% yttrium had an acceptable elongation.

Alloy 12 illustrates the importance of keeping the difference between the sum of the tungsten and molybdenum concentrations and the sum of the ruthenium, niobium and zirconium concentrations below about 5%. This difference for alloy 12 is not below 5% and the alloy has an unacceptable elongation of 3%. Alloy 5, on the other hand, has the same composition as alloy 12, but with 2 percent of the tungsten replaced by niobium, and this alloy has an acceptable elongation of 6%. The difference between the sum of the tungsten and molybdenum concentrations and the sum of the ruthenium, niobium and zirconium concentrations for alloy 5 is less than 5%.

Although specific embodiments of the invention have been described and illustrated, it is to be understood that modifications can be made without departing from the invention's spirit and scope. Thus the concentrations of cobalt, chromium, ruthenium, aluminum, yttrium, tungsten, molybdenum, niobium, zirconium and manganese can be varied from the percentages illustrated and alloys having the superior characteristics of the invention will still result. For example, the cobalt concentration can be varied at least between 40 and 60%; the chromium concentration between 20 and 30%; the ruthenium concentration between 5 and 15%; the aluminum concentration between 1 and 4%; the yttrium concentration between 0 and 0.15%; the tungsten concentration between 0 and 15%; the molybdenum concentration between 0 and 6.5%; the niobium concentration between 0 and 3.0%; the zirconium concentration between 0 and 0.25%; and the manganese concentration between 0 and 1.5%.

What is claimed is:

1. A cobalt-chromium dental alloy for use in porcelain-fused-to-metal restorations consisting essentially of about:

| Element | Weight Percent |
|---|---|
| Cobalt | 40-60 |
| Chromium | 20-30 |
| Ruthenium | 5-15 |
| Aluminum | 1-4 |
| Yttrium | 0-0.15 |
| Tungsten | 0-15 |
| Molybdenum | 0-6.5 |
| Niobium | 0-3.0 |
| Zirconium | 0-0.25 |
| Manganese | 0-1.5 | wherein the sum of the constituents equals 100%, the sum of the tungsten and molybdenum constituents minus the sum of the ruthenium, niobium and zirconium constituents is less than about 5% and the alloy is both nickel and beryllium free.

2. A cobalt-chromium dental alloy for use in porcelain-fused-to-metal restorations consisting essentially of about 54.85% cobalt, 25% chromium, 5% ruthenium, 2.9% aluminum, 0.1% yttrium, 10% tungsten, 2% niobium, and 0.15% zirconium, wherein the alloy is both nickel and beryllium free.

3. A cobalt-chromium dental alloy for use in porcelain-fused-to-metal restorations consisting essentially of about 53% cobalt, 23% chromium, 10% ruthenium, 3.9% aluminum, 0.1% yttrium, and 10% tungsten, wherein the alloy is both nickel and beryllium free.

4. A cobalt-chromium dental alloy for use in porcelain-fused-to-metal restorations consisting essentially of about 55% cobalt, 25% chromium, 5% ruthenium, 2.9% aluminum, 0.1% yttrium, 10% tungsten, and 2% niobium, wherein the alloy is both nickel and beryllium free.

5. A cobalt-chromium dental alloy for use in porcelain-fused-to-metal restorations consisting essentially of about 60% cobalt, 25% chromium, 5% ruthenium, 3.9% aluminum, 0.1% yttrium, 5% molybdenum, and 1.0% manganese, wherein the alloy is both nickel and beryllium free.

* * * * *